United States Patent [19]

Hale et al.

[11] Patent Number: 4,958,034

[45] Date of Patent: Sep. 18, 1990

[54] ALKENYL SUCCINIC ANHYDRIDES PROCESS

[75] Inventors: Paul S. Hale; Kju H. Shin, both of Baton Rouge, La.

[73] Assignee: Ethyl Corporation, Richmond, Va.

[21] Appl. No.: 436,072

[22] Filed: Nov. 13, 1989

[51] Int. Cl.$^5$ .......................................... C07D 307/60
[52] U.S. Cl. ..................................... 549/255; 549/203
[58] Field of Search ................................ 549/255, 203

[56] References Cited

U.S. PATENT DOCUMENTS 3,775,436  11/1973  Stenseth .............................. 549/203
4,028,264  6/1977  Puskas et al. .................... 252/182.18

*Primary Examiner*—Mary C. Lee
*Assistant Examiner*—Bernard I. Dentz
*Attorney, Agent, or Firm*—Joseph D. Odenweller

[57] ABSTRACT

Alkenyl succinic anhydrides having a decreased amount of tar and color bodies are made by the reaction of an olefin with maleic anhydride in the presence of an arylfluorophosphite (e.g. 2,2'-ethylidenebis(4,6-di-tert-butylphenyl) fluorophosphite) and optionally a hindered phenolic antioxidant such as 2,4,6-tri(3,5-di-tert-butyl-4-hydroxybenzyl) mesitylene.

20 Claims, No Drawings

ALKENYL SUCCINIC ANHYDRIDES PROCESS

BACKGROUND

Alkenyl succinic anhydrides ("ASA") are used as paper sizing agents, bleach activators and as corrosion inhibitors and detergents in petroleum products. They are also readily converted to derivatives such as esters, amides and imides useful in petroleum products.

The thermal process of making ASA requires heating of an olefin and maleic anhydride ("MA") to fairly high temperatures on the order of 175°-275° C. If desired the reaction can be promoted by addition of chlorine. Some degradation occurs in the reaction mixture caused by homopolymerization of MA and copolymerization of MA and olefin leading to discoloration and formation of tar and particulates. These decomposition products have an adverse effect on the performance of ASA in many of its leading markets such as paper size.

Attempts have been made to inhibit the formation of tar in the reaction of olefin with MA. Key et al., GB No. 1,337,724, describe the use of certain phosphorus-containing sequestrants and hydroxy aromatics to inhibit tar formation in making ASA for use as a detergent builder.

Irwin et al., U.S. Pat. No. 3,412,111, describe the use of hydroxy aromatics, e.g. hydroquinone, and amino aromatics, e.g. phenothiazine, to inhibit polymer formation during preparation of ASA.

Puskas et al., U.S. Pat. No. 3,935,249, disclose the use of small amounts of inorganic halogen compound such as dry HCl or calcium bromide to prevent tar formation.

Zaweski et al., U.S. Pat. No. 3,476,774, report the use of hindered phenols, e.g. 4,4'-methylenebis(2,6-di-tert-butylphenol) and 1,3,5-trimethyl-2,4,6-tri(3,5-di-tert-butyl-4-hydroxybenzyl) benzene, to prevent decomposition of the reactants.

Kao Soap in Japan No. 56/12382 describe the use of organic phosphite esters, e.g. tributyl phosphite, in making ASA. Japan No. 60/78975 report the use of a combination of trialkyl phosphite, e.g. trioctyl phosphite, and dihydroxy aromatic, e.g. 2,5-di-tert-butylhydroquinone, in the preparation of ASA.

SUMMARY

It has now been discovered that greater reduction in the amount of discoloration and tar formation can be achieved by preparing ASA in the presence of an arylfluorophosphite.

DESCRIPTION OF THE PREFERRED EMBODIMENTS

A preferred embodiment of the invention is a process for making an alkenyl succinic anhydride having reduced levels of tar and color bodies, said process comprising reacting maleic anhydride with an aliphatic olefin containing about 4-250 carbon atoms at a temperature of about 190°-250° C. in the presence of a stabilizing amount of an arylfluorophosphite, said arylfluorophosphite being characterized by having at least one substituted or unsubstituted aryloxy group and at least one fluorine atom bonded directly to a trivalent phosphorus atom.

Arylfluorophosphites are compounds that have at least one aryloxy group bonded to a trivalent phosphorus atom and at least one fluorine atom bonded directly to the same phosphorus atom. Examples are diphenyl fluorophosphite, phenyl difluorophosphite, 2-naphthyl methyl fluorophosphite, 2-methylphenyl n-propyl fluorophosphite, 2-tert-butyl-4-methylphenyl sec-dodecyl fluorophosphite, 2,4,6-trimethylphenyl difluorophosphite, 2,4-di-sec-butylphenyl difluorophosphite, 1-naphthyl phenyl fluorophosphite, 7-indenyl 4-methylphenyl fluorophosphite, 4-tert-butylphenyl difluorophosphite, di(2-methyl-6-tert-butylphenyl) fluorophosphite and the like.

In a more preferred embodiment, the aryloxy group(s) bonded to phosphorus is a substituted aryloxy group having the structure

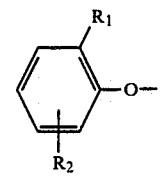

I wherein $R_1$ is selected from the group consisting of alkyl groups containing 1 to about 20 carbon atoms, cycloalkyl groups containing 5-8 carbon atoms, and aralkyl groups containing 6-2 carbon atoms and $R_2$ is selected from hydrogen or the same group as $R_1$.

Some examples of these more preferred arylfluorophosphites are di-(2-tert-butylphenyl) fluorophosphite, 2-isopropyl-4-methylphenyl difluorophosphite, 2-sec-butylphenyl difluorophosphite, 2-(1-methyldecyl)-4-cyclopentylphenyl difluorophosphite, 2-sec-eicosyl-4-methylphenyl difluorophosphite, 2,4-dicyclohexylphenyl difluorophosphite, 2-cyclopentyl-4-ethylphenyl difluorophosphite, di-(2-cyclooctylphenyl) fluorophosphite, di-(2-benzylphenyl) fluorophosphite, 2-(α-methylbenzyl)-4-methyl phenyl difluorophosphite, di-[2,4-di-(α-methylbenzyl)phenyl]fluorophosphite, 2-(α,α-dimethylbenzyl) phenyl difluorophosphite, 2,6-dibenzylphenyl difluorophosphite, 2-(α-methyl-4-isopropylbenzyl) phenyl difluorophosphite and the like.

In a highly preferred embodiment, the arylfluorophosphite has the structure

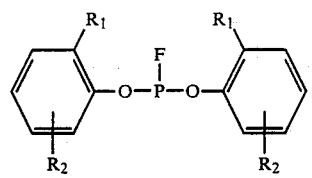

II wherein $R_1$ and $R_2$ are as previously defined. The $R_1$ substituents on the phenyl groups need not be the same. Likewise $R_2$ substituents on the phenyl groups need not both be the same. Examples of these compounds are di(2,4-dimethylphenyl) fluorophosphite, di(2,4-diisopropylphenyl) fluorophosphite, di[2-(α-methylbenzyl)-phenyl]fluorophosphite, di(2,6-dicyclohexylphenyl) fluorophosphite, di(2-benzylphenyl) fluorophosphite, di(2-methyl-4-tert-octylphenyl) fluorophosphite and the like.

More preferably, $R_1$ is a tert-alkyl group containing 4-20 carbon atoms. Still more preferably, both $R_1$ and $R_2$ are tert-alkyl groups containing 4-20 carbon atoms and $R_2$ is bonded at an ortho or para position on the benzene ring. Example of these are di(2-tert-butylphenyl) fluorophosphite, di(2,4-di-tertoctylphenyl) fluorophosphite, di(2-tert-dodecylphenyl) fluorophosphite, di(2,6-di-tert-hexylphenyl) fluorophosphite, di(2-tert-butyl-4-tert-hexylphenyl) fluorophosphite, di(2,4-di-tertpentylphenyl) fluorophosphite, di(2,4-di-tert-eicosylphenyl) and the like.

In a further preferred embodiment, both $R_1$ and $R_2$ in Formula II are tert-butyl groups. These compounds are di(2,6-di-tert-butylphenyl) fluorophosphite, di(2,4-di-tert-butylphenyl) fluorophosphite and 2,4-di-tert-butyl-phenyl 2,6-di-tert-butylphenyl fluorophosphite. Another preferred class of arylfluorophosphites are the cyclic di-aryl fluorophosphites in which the two aryl groups are bridged to each other at an ortho position. These are represented by the structure

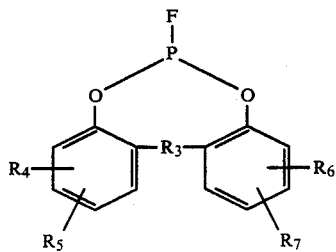

III wherein $R_3$ is a divalent group selected from —$S_x$— wherein x is an integer from 1 to 3, methylene or alkylidene containing 2–12 carbon atoms or $R_3$ is absent forming a direct single bond between the two phenyl groups and $R_4$, $R_5$, $R_6$ and $R_7$ are independently selected from hydrogen, alkyl groups containing 1–20 carbon atoms, cycloalkyl groups containing 5–8 carbon atoms or aralkyl groups containing 7–12 carbon atoms. A more preferred class of the cyclic diaryl fluorophosphites are those represented by the formula

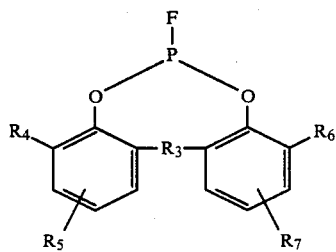

IV wherein $R_4$ and $R_6$ are tert-alkyl groups containing 4–20 carbon atoms and $R_3$, $R_5$ and $R_6$ are as previously defined. Some examples are 2,2'-methylenebis(6-tert-butylphenyl) fluorophosphite, 2,2'-ethylidenebis(4,6-di-tert-dodecylphenyl) fluorophosphite, 2,2'-isopropylidenebis(6-tert-octylphenyl) fluorophosphite, 2,2'-thiobis(4,6-di-tert-butylphenyl) fluorophosphite, 2,2'-dithiobis(4-tert-eicosyl-6-methylphenyl) fluorophosphite, 2,2'-butylidenebis(4-methyl-6-tert-eicosylphenyl) fluorophosphite, 2,2'-bis(6-tert-butylphenyl) fluorophosphite, 2,2'-bis(4-methyl-6-tert-octylphenyl) fluorophosphite, 2,2'-bis(4-sec-octadecyl-6-tert-decylphenyl) fluorophosphite and the like.

In Formula IV, it is more preferred that $R_5$ and $R_7$ are alkyl groups containing 1–20 carbon atoms and are bonded to the para position. Still more preferably $R_5$ and $R_7$ are tertalkyl groups containing 4–20 carbon atoms and are bonded to the para position. Examples of these compounds are 2,2'-thiobis(4,6-di-tert-butylphenyl) fluorophosphite, 2,2'-thiobis(4,6-di-terthexylphenyl) fluorophosphite, 2,2'-thiobis(4,6-di-tert-octylphenyl) fluorophosphite, 2,2'-bis(4,6-di-tert-butylphenyl) fluorophosphite, 2,2'-bis(4-tert-butyl-6-tert-dodecylphenyl) fluorophosphite, 2,2'-bis(4,6-di-tert-eicosylphenyl) fluorophosphite, 2,2'-methylenebis(4-tert-butyl-6-tert-octylphenyl) fluorophosphite, 2,2'-methylenebis(4,6-di-tert-eicosylphenyl) fluorophosphite, 2,2'-ethylidenebis(4,6-di-tert-octylphenyl) fluorophosphite, 2,2'-ethylidenebis(4-tert-butyl-6-tert-dodecylphenyl) fluorophosphite, 2,2'-isopropylidenebis(4,6-di-tert-butylphenyl) fluorophosphite, 2,2'-butylidenebis(4,6-di-tert-butylphenyl) fluorophosphite, 2,2'-dodecylidenebis(4,6-di-tert-butylphenyl) fluorophosphite and the like.

The most preferred arylfluorophosphite is 2,2'-ethylidenebis(4,6-di-tert-butylphenyl) fluorophosphite.

The arylfluorophosphites can be made by preparing the corresponding arylchlorophosphite and conducting a halogen exchange reaction with an alkali metal fluoride, e.g. NaF, KF. This can be catalyzed by a small amount of pyridine and/or HF. The arylchlorophosphites are known compounds and are readily made by reacting PCl$_3$ with a phenolic compound in a mole ratio of about 1.0:1.0–2.0. This reaction can be promoted by the addition of an amine or pyridine.

The alkenyl succinic anhydrides (ASA) are made by heating a mixture of maleic anhydride (MA) and aliphatic olefin at a temperature of about 175–275° C. The molecular weight of the olefin can vary widely depending upon the intended use of the ASA. Paper size ASA have an alkenyl group of about 12–24 carbon atoms. Corrosion inhibitors and fuel detergents generally have an alkenyl group of about 16–35 carbon atoms. ASA used to make imides, amides and esters for use as lubricating oil dispersants have an alkenyl group of about 40–250 carbon atoms. With the very high molecular weight ASAs, it is more accurate to refer to number average molecular weight ($\overline{Mn}$) since the olefins used to make these ASAs are a mixture different molecular weight components resulting from the polymerization of low molecular weight olefin monomers such as ethylene, propylene and isobutylene.

The olefins may be linear or branched. For example, olefins derived from triethyl aluminum/ethylene chain growth via so-called Ziegler chemistry are mainly linear o-olefins. Olefins derived from the polymerization of isobutylene have repeating methyl branching. Both are useful in the present process.

Internal olefins such as those made by isomerizing α-olefins or by dimerizing o-olefins. For example, isomerized C$_{16-18}$ α-olefin forms an ASA having excellent paper sizing properties. Likewise the aluminum alkyl catalyzed dimerization of C$_{8-12}$ α-olefins forms C$_{16-24}$ vinylidene olefins that can be used to make useful ASA paper size.

The reaction is carried out by heating a mixture of MA, an olefin and a small amount of an arylfluorophosphite to a reaction temperature of about 150°–300° C., more preferably 175°–275° C. and most preferably 200°–250° C. The reaction is preferably conducted in a sealed reaction vessel under autogenous pressure to prevent loss of reactants. Maleic anhydride boils at 202° C.

The mole ratio of MA to olefin can vary widely. It can vary, for example, from 5:1 to 1:5. A more preferred range is 3:1 to 1:3. With the high molecular weight olefins such as polyisobutylene having a number average molecular weight of 900–5000 or higher, the MA is preferably used in stoichiometric excess, e.g. 1.1-5 moles MA per mole of olefin. The unreacted MA can be vaporized from the resultant reaction mixture.

With the lower molecular weight olefins as used in making paper size and corrosion inhibitors, e.g. Mn of 200-350, either can be used in excess or they can be reacted in a 1:1 mole ratio. Usually an excess of olefin is used, e.g. 1.1-3 moles olefin per mole MA.

The amount of arylfluorophosphite is a small but effective amount. The optimum amount can easily be determined experimentally by gradually increasing the amount of arylfluorophosphite until the color and tar formation decreases to the desired amount. A useful range in which to conduct these experiments is about 0.05-2.0 weight percent based on the weight of MA charged. A more preferred amount is about 0.1-1.0 weight percent of the amount of maleic anhydride charged.

EXAMPLE 1

Preparation of 2,2'-ethylidenebis(4,6-di-t-butylphenyl) chlorophosphite

Under a nitrogen atmosphere, 117 ml of phosphorus trichloride and 1.3 l of toluene were combined and the admixture was cooled to 5° C. A solution of 573 grams of 2,2'-ethylidenebis(4,6-di-t-butylphenol), 375 ml of triethylamine, and 2.0 l of toluene was added dropwise to the admixture over a period of 6 hours. The reaction mixture was maintained below a temperature of 10° C. during the addition. Next, the reaction mixture was allowed to warm to ambient temperature. The product was a toluene solution of 2,2'-ethylidenebis(4,6-di-tert-butylphenyl) chlorophosphite.

Transhalogenation Reaction

After 1 hour at ambient temperature, 135 grams of antimony trifluoride was added to the above mixture to form a slurry. The slurry was warmed to 85° C. over a period of 1 hour and maintained at this temperature for 4 hours. The crude reaction product comprised a pale green organic layer over a thick green oil. The pale green organic layer was decanted from the oil. The organic layer was filtered through 165 grams of silica gel 60. The filter cake was then washed with toluene. The clear colorless filtrates were concentrated under vacuum to 617 grams of white solids. By quantitative P-NMR, the solids were determined to be a 4:1 mixture of the two possible diasteriomers of 2,2'-ethylidenebis(4,6-di-tert-butylphenyl) fluorophosphite. An analysis by H-NMR, P-NMR, F-NMR and MS was consistent with these structures.

EXAMPLE 2

The 2,2'-ethylidenebis(4,6-di-tert-butylphenyl) chlorophosphite starting material was made by heating a mixture of 1300 grams of 2,2'-ethylidenebis(4,6-di-tert-butylphenol), 2 liters of xylene and 13 grams of pyridine in a reaction vessel to 100° C. while maintaining a nitrogen sweep over the reaction surface to assist in HCl removal and thereafter slowly adding 500 grams of PCl$_3$ to the reaction mixture over a period of 45 minutes. The mixture was then stirred and heated to 135° C. Stirring was continued for 1.5 hours at 135° C. under nitrogen and then allowed to cool to 10° C. The resultant solid was collected by filtration and 500 grams of the filter cake (1484 grams total weight) was washed with 500 grams of xylene and dried at about 80° C. under vacuum overnight. Conversion to 2,2'-ethylidenebis(4,6-di-tertbutylphenyl) chlorophosphite was essentially complete. Analysis by GC (gas chromatography) showed 98 area percent 2,2'-ethylidenebis(4,6-di-tert-butylphenyl) chlorophosphite and 2.0 percent 2,2'-ethylenebis(4,6-di-tert-butylphenyl) hydrogenphosphonate.

To 10 grams of this product mixture dissolved in 18 grams of xylene and heated to 90-95° C., there was added incrementally, under nitrogen, 2.0 grams of pyridine hydrofluoride (0.02 mol HF; 19.7 wt. % HF) over a period of approximately 170 minutes.

The product mixture was allowed to cool overnight, reheated to 90-95° C. the following morning and analyzed by GC to be 92.4 area percent 2,2'-ethylidenebis(4,6-di-tert-butylphenyl) fluorophosphite, 0.6 percent 2,2'-ethylidenebis(4,6-di-tertbutylphenyl) chlorophosphite and 6.7 percent 2,2'-ethylenebis(-4,6-di-tert-butylphenyl) hydrogenphosphonate.

The following examples show the preparation of several more arylfluorophosphites that find use in the present process.

EXAMPLE 3

Preparation of bis(2,4-di-t-butylphenyl) fluorophosphite

Under a nitrogen atmosphere, 6 ml of phosphorus trichloride and 100 ml of anhydrous tetrahydrofuran were combined and the admixture was cooled below 10° C. A solution of 28.7 grams of 2,4-di-t-butylphenol, 20 ml of triethylamine, and 150 ml of anhydrous tetrahydrofuran was added dropwise to the admixture over a period of 80 minutes. The resulting slurry was allowed to warm to ambient temperature. After 2 hours at ambient temperature, 8 grams of antimony trifluoride was added to the slurry. The slurry was then heated to reflux temperature and maintained at this temperature for 1 hour. The slurry was allowed to cool and then filtered through basic aluminum oxide. The filter cake was washed with toluene. The filtrates were concentrated under vacuum to 30.8 grams of a pale yellow oil. A 27 gram portion of the crude product was dissolved in 150 ml of n-heptane and filtered to remove insoluble materials. The filtrate was concentrated to 25 grams of a pale yellow oil. The oil was next stirred with 100 ml of acetonitrile. The white solid which was formed was collected by filtration to yield 17.5 grams of bis(2,4-di-t-butylphenyl) fluorophosphite. The H-NMR, P-NMR, F-NMR and MS of the solid were consistent with this structure.

EXAMPLE 4

Preparation of 4,4'-methylenebis(2,6-di-tert-butylphenyl) tetrafluorodiphosphite In a reaction vessel under nitrogen was placed 10.7 grams of 4,4'-methylenebis(2,6-di-tert-butylphenol), 4.4 ml of PCl$_3$, 7 ml of triethylamine and 100 ml of toluene. The mixture was heated at 50° C. with stirring for 5.5 hours. It was then heated to 80° C. and held at 80° C. for 36 hours. Then 7.2 grams of SbF$_3$ was added and the mixture stirred 4.5 hours at 80° C. and then cooled. Two phases formed. The upper yellow liquid phase was decanted and filtered through silica gel and the filtrate was evaporated to give 11.4 grams residue which solidified to a yellow waxy solid. The crude product was recrystallized from acetonitrile to obtain a white solid (mp. 125-26° C.). The H-NMR, P-NMR were consistent with the target tetrafluorodiphosphite.

EXAMPLE 5

Preparation of 2.2'-bis(4.6-di-tert-butylphenyl) fluorophosphite

Under a nitrogen atmosphere a solution of 8.2 grams of 4,4',6,6'-tetra-tert-butyl-2,2'-biphenyl and 5.9 ml of triethylamine in 25 ml of toluene was added to a cooled (5° C.) solution of 1.8 ml of $PCl_3$ in 20 ml of toluene over a 1.25 hour period. At the end of the addition, the slurry was stirred 15 minutes and the mixture then warmed to ambient temperature. After stirring overnight, 2.0 grams of $SbF_3$ was added. The resulting slurry was heated to and maintained at 85° C. for 6.5 hours. After cooling, the toluene layer was decanted from the black solid residue and filtered through Celite. The filtrate was evaporated to give about 9 grams of a yellow oil. The yellow oil was washed with acetonitrile and purified by column chromatography in a n-heptane solvent. The product recovered from the eluant was a white solid with a m.p. of 188° C. The P-NMR showed a 1300 Hz doublet at 132.4 ppm (from $H_3PO_4$, $CDCl_3$) which confirmed the identify of the product as the target compound.

The following example shows the preparation of an ASA without use of an arylfluorophosphite and is for comparative purposes.

EXAMPLE 6

In an autoclave was placed 60.71 g of mixed $C_{16}/C_{18}$ internal olefins (made by isomerizing the corresponding α-olefins) and 12.46 g of MA. The autoclave was purged with nitrogen, sealed and heated while stirring to 230° C. (two minutes heat-up). After 5 hours total reaction time the autoclave was cooled and discharged to obtain a dark orange product containing some black solids (Gardner Color 11.5). The product was distilled under vacuum using a Kugel-Rohr apparatus to remove unreacted olefin, MA and ASA having a polymeric residue equal to 15.7 weight percent of the reaction mixture.

The following example shows the use of an arylfluorophosphite in the present process.

EXAMPLE 7

In an autoclave was placed 80.81g $C_{16}/C_{18}$ mixed internal olefins, 16.59 g MA and 0.125 g 2,2'-ethylidenebis(4,-6-di-tert-butylphenyl) fluorophosphite. The autoclave was purged with nitrogen, sealed and while stirring, heated to 230° C. over a 25-minute period. Stirring was continued at 230° C. to give a total 5-hour reaction time from start of heating. The autoclave was cooled and discharged to give bright yellow-orange product having a Gardner color of 8.5. After Kugel-Rohr distillation the residue was 7.4 weight percent.

EXAMPLE 8

In an autoclave was placed 83.37 g mixed $C_{16}/C_{18}$ internal olefins, 17.12 g MA and 0.1285 g bis(2-tert-butyl-6-methylphenyl) fluorophosphite. The autoclave was purged with nitrogen, sealed and stirred while heating to 230° C. After a total 5-hour reaction period, the autoclave was cooled and discharged. The color was yellow with medium to light varnish formation and very little solids. The Gardner color was 6.5 and the residue after distillation was 9.1.

The following example shows that not all phosphites are effective in the process and is for comparative purposes.

EXAMPLE 9

In an autoclave was placed 83.51 g of mixed $C_{16}/C_{18}$ internal olefins, 17.16 g MA and 0.1287 g tributyl phosphite. The autoclave was flushed with nitrogen, sealed and stirred while heating to 230° C. After a 5-hour total reaction period the autoclave was cooled and discharged. The product was orange and contained many black specks. The interior of the autoclave was heavily varnished. The Gardner color of the reaction product was 10.5 and the residual was 6.9 weight percent.

EXAMPLE 10

In an autoclave was placed 81.62 g mixed $C_{16}/C_{18}$ internal olefins (same source as Example 1), 16.7 g MA and 0.126 g of triphenyl phosphite. The autoclave was flushed with nitrogen, sealed and while stirring heated to 230° C. as in Example 1. The autoclave was then cooled and discharged to give a light yellow product (Gardner Color 6.0). The product was distilled as in Example 6 to give 12.0 weight percent residual polymer.

The following table compares the color and polymeric residue obtained in the examples.

| Example | Additive | Gardner Color | Polymeric Residue |
|---|---|---|---|
| 6 | None | 11.5 | 15.7 |
| 7 | 2,2'-ethylidenebis(4,6-di-tert-butylphenyl)fluorophosphite | 8.5 | 7.4 |
| 8 | bis(2-tert-butyl-6-methylphenyl fluorophosphite | 6.5 | 9.1 |
| 9 | tributyl phosphite | 10.5 | 6.9 |
| 10 | triphenyl phosphite | 6.0 | 12.7 |

The test results show that the arylfluorophosphites of the present invention (Examples 7 and 8) were the only additives to give both a low Gardner color and a low polymer residue. The arylfluorophosphites can be used alone in the process or they can be used in combination with hindered phenolic antioxidants including all those disclosed in Zaweski et al., U.S. Pat. No. 3,476,774, (incorporated herein by reference). These include 4,4'-methylenebis(2,6-di-tert-butylphenyl, pentaerythritol tetrakis [3-(3,5-di-tert-butyl-4-hydroxyphenyl)propionate], 2,4,6-tri(3,5-di-tert-butyl-4-hydroxybenzyl) mesitylene, and the

We claim:

1. A process for making an alkenyl succinic anhydride having reduced levels of tar and color bodies, said process comprising reacting maleic anhydride with an aliphatic olefin containing about 4–250 carbon atoms at a temperature of about 190°–250° C. in the presence of a stabilizing amount of an arylfluorophosphite, said arylfluorophosphite being characterized by having at least one substituted or unsubstituted aryloxy group and at least one fluorine atom bonded directly to a trivalent phosphorus atom.

2. A process of claim 1 wherein said aryloxy group has the structure

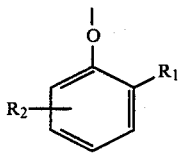

wherein R₁ is selected from the group consisting of alkyl groups containing 1 to about 20 carbon atoms, cycloalkyl groups containing 5-8 carbon atoms and aralkyl groups containing 6-12 carbon atoms and R₂ is selected from hydrogen or the same group as R₁.

3. A process of claim 2 wherein said arylfluorophosphite has the structure:

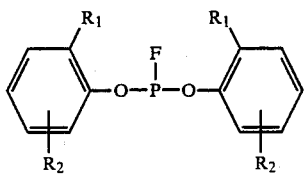

wherein R₁ and R₂ are as previously defined.

4. A process of claim 3 wherein R₁ is a tert-alkyl group containing 4-20 carbon atoms.

5. A process of claim 4 wherein R₁ is a tert-butyl

6. A process of claim 5 wherein R₂ is a tert-alkyl group containing 4-20 carbon atoms.

7. A process of claim 6 wherein R₂ is a tert-butyl

8. A process of claim 7 wherein R₂ is bonded to an ortho position.

9. A process of claim 8 wherein R₂ is bonded to the para position.

10. A process of claim 1 wherein said arylfluorophosphite has the structure

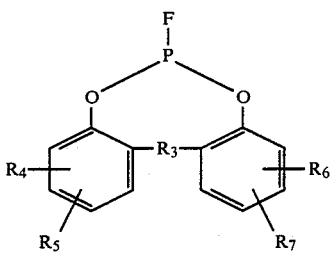

wherein R₃ is a divalent group selected from —S$_x$— wherein x is an integer from 1 to 3, methylene or alkylidene containing 2-12 carbon atoms or R₃ is absent forming a direct single bond between the two phenyl groups and R₄, R₅, R₆ and R₇ are independently selected from hydrogen, alkyl groups containing 1-20 carbon atoms, cycloalkyl groups containing 5-8 carbon atoms or aralkyl groups containing 7-12 carbon atoms.

11. A process of claim 10 wherein said arylfluorophosphite has the structure

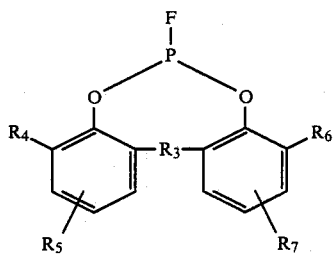

wherein R₄ and R₆ are tert-alkyl groups containing 4-20 carbon atoms and R₃, R₅ and R₇ are as previously defined.

12. A process of claim 11 wherein R₅ and R₇ are tert-alkyl groups containing 4-20 carbon atoms and are bonded to the para positions of the aryl group.

13. A process of claim 12 wherein said arylfluorophosphite is 2,2'-ethylidenebis(4,6-di-tert-butylphenyl) fluorophosphite.

14. A process of claim 12 wherein said arylfluorophosphite is 2,2'-methylenebis(4,6-di-tert-butylphenyl) fluorophosphite.

15. A process of claim 12 wherein said arylfluorophosphite is 2,2'-bis(4,6-di-tert-butylphenyl) fluorophosphite.

16. A process of claim 1 conducted in the co-presence of a hindered phenolic antioxidant.

17. A process of claim 16 wherein said arylfluorophosphite is 2,2'-ethylidenebis(4,6-di-tert-butylphenyl) fluorophosphite.

18. A process of claim 17 wherein said hindered phenolic antioxidant is 2,4,6-tri(3,5-di-tert-butyl-4-hydroxybenzyl) mesitylene.

19. A process of claim 17 wherein said hindered phenolic antioxidant is pentaerythritol tetrakis[3-(3,5-di-tert-butyl-4-hydroxyphenyl) propionate].

20. A process of claim 17 wherein said aliphatic olefin is a hydrocarbon containing about 12-24 carbon atoms.

* * * * *

UNITED STATES PATENT AND TRADEMARK OFFICE
CERTIFICATE OF CORRECTION

PATENT NO. : 4,958,034
DATED : SEPTEMBER 18, 1990
INVENTOR(S) : PAUL S. HALE ET AL.

It is certified that error appears in the above-identified patent and that said Letters Patent is hereby corrected as shown below:

Column 9, line 29 reads "is a tert-butyl" and should read
-- is a tert-butyl group. -- .

Column 9, line 33 reads "is a tert-butyl" and should read
-- is a tert-butyl group. -- .

Signed and Sealed this

Twenty-sixth Day of November, 1991

Attest:

HARRY F. MANBECK, JR.

Attesting Officer   Commissioner of Patents and Trademarks